United States Patent [19]

Cöllin et al.

[11] 4,266,082
[45] May 5, 1981

[54] PREPARATION OF 4-FLUORO-3-PHENOXY-TOLUENE

[75] Inventors: Reimer Cöllin; Hans-Joachim Diehr, both of Wuppertal; Uwe Friesnitz, Unna-Massen, all of Fed. Rep. of Germany

[73] Assignee: Bayer Aktiengesellschaft, Leverkusen, Fed. Rep. of Germany

[21] Appl. No.: 67,649

[22] Filed: Aug. 17, 1979

[30] Foreign Application Priority Data

Aug. 28, 1978 [DE] Fed. Rep. of Germany ....... 2837525

[51] Int. Cl.³ ............................................. C07C 41/01
[52] U.S. Cl. ......................................... 568/639; 560/9; 560/20; 560/61; 560/105; 560/124; 260/465 D; 260/340.5 R; 260/465 F
[58] Field of Search ........................................ 568/639

[56] References Cited
U.S. PATENT DOCUMENTS

| 3,637,866 | 1/1972 | De Pasquale et al. | 260/612 R |
| 3,966,453 | 6/1976 | Takahashi et al. | 568/639 X |
| 4,124,370 | 11/1978 | Yu | 71/78 |

FOREIGN PATENT DOCUMENTS

| 2242519 | 3/1974 | Fed. Rep. of Germany . |
| 2619489 | 11/1976 | Fed. Rep. of Germany . |
| 2709264 | 7/1978 | Fed. Rep. of Germany . |

OTHER PUBLICATIONS

Houben-Weyl, vol. 6/3, (1965), p. 87.

Weingarten, Jour. Org. Chem., vol. 29 (1964), 977-978.

Primary Examiner—Bernard Helfin
Attorney, Agent, or Firm—Sprung, Felfe, Horn, Lynch & Kramer

[57] ABSTRACT

A process for the preparation of 4-fluoro-3-phenoxy-toluene of the formula

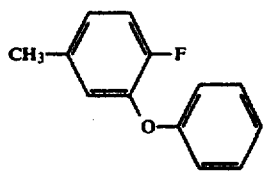

comprising reacting 3-bromo-4-fluoro-toluene, of the formula

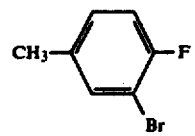

with potassium phenolate, or with sodium phenolate in the presence of a potassium salt, in a diluent in the presence of copper as catalyst at a temperature between about 120° and 180° C.

14 Claims, No Drawings

PREPARATION OF 4-FLUORO-3-PHENOXY-TOLUENE

The invention relates to a novel process for the preparation of 4-fluoro-3-phenoxy-toluene.

Reactions of halogeno-fluoro-benzene derivatives with alcoholates or phenolates, in which fluorine is replaced in preference to the other halogens, have been disclosed. Thus, for example, 4-fluoro-chloro-benzene and potassium phenolate give, as the main product, 4-chloro-diphenyl ether (See DE-OS [German Published Specification] No. 2,619,489). The reaction of chloro-pentafluoro-benzene with sodium pentafluorophenolate gives an isomer mixture of 4-chloro-nonafluoro-diphenyl ether and 2-chloro-nonafluoro-diphenyl ether (See U.S. Pat. No. 3,637,866).

Bromo-2,3,4,6-tetrafluoro-benzene reacts with sodium methylate to give an isomer mixture of bromo-trifluoro-methoxybenzenes (See J. Chem. Soc. Perkin Trans. II 1978, pages 137–141).

Several processes for the preparation of 3-phenoxy-toluene by reacting bromobenzene with m-cresolate are known; however, this does not present the problem of the selective replacement of one of two different halogen substituents (See British Patent Specification No. 1,052,390 and DE-OS [German Published Specification] No. 2,619,489).

Further, it is known that it can be advantageous to carry out the preparation of diphenyl ethers from halogeno-benzenes and phenolates in the presence of potassium salts (See DE-OS [German Published Specification] No. 2,242,519).

The present invention now provides a process for the preparation of 4-fluoro-3-phenoxy-toluene, of the formula

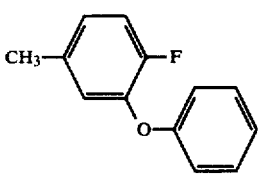

(I), in which 3-bromo-4-fluoro-toluene, of the formula

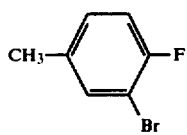

(II), is reacted with potassium phenolate, or with sodium phenolate in the presence of a potassium salt, in either case in the presence of copper or of a catalytically active copper compound, using a diluent, at a temperature between about 120° and 180° C.

It is surprising that using the process according to the invention virtually only 4-fluoro-3-phenoxy-toluene is produced from 3-bromo-4-fluoro-toluene and the phenolate, since rather, according to the prior art, a replacement of the fluorine, with formation of 3-bromo-4-phenoxy-toluene, would have been expected.

Advantages of the new process are the relative simplicity with which it can be carried out, and the good yield and high purity of the product.

The reaction according to the invention can be outlined by the following equation:

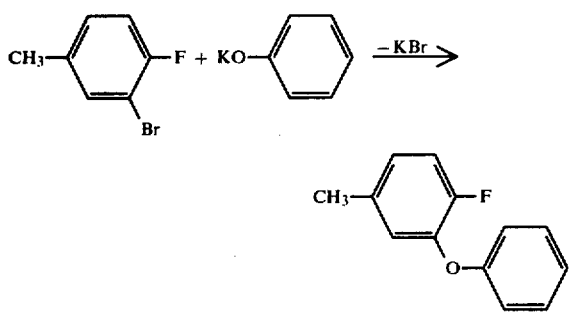

3-Bromo-4-fluoro-toluene, to be used as the starting compound, is already known (See Canad. Journ. Chem. 38 (1960), 2,441–2,449).

The process according to the invention is in general carried out in the presence of a diluent. Suitable diluents are, above all, aprotic polar solvents. These include, in particular, carboxylic acid amides, for example dimethylformamide, dimethylacetamide and N-methylpyrrolidone, sulphoxides and sulphones, for example dimethylsulphoxide and tetramethylenesulphone, and phosphoric acid amides, for example hexamethylphosphorotriamide. Dimethylacetamide has proved particularly suitable.

The catalysts used are copper, or copper compounds of various oxidation levels. Copper, copper(I) oxide, copper(II) oxide, copper(I) chloride, copper(II) chloride, copper(I) bromide copper(II) bromide and copper(I) iodide may be mentioned as examples.

The reaction temperature in the process according to the invention is in general between 120° and 180° C., preferably about 130° to 170° C. The reaction is in general carried out under normal pressure.

When working with potassium phenolate, in general between 1.5 and 8 moles, preferably about 2 to 4 moles, of potassium phenolate are employed per mole of 3-bromo-4-fluoro-toluene. In a particular embodiment of the process, the potassium phenolate is prepared in situ from equimolar amounts of potassium hydroxide and phenol before the reaction with 3-bromo-4-fluoro-toluene. The reaction is in general carried out in one of the stated diluents, in the presence of one of the stated catalysts; in general between 0.001 and 0.1 mole, preferably about 0.005 to 0.05 mole, of catalyst is employed in the reaction per mole of 3-bromo-4-fluoro-toluene. The reaction mixture is stirred for several hours, in general for between three and five hours, at the required temperature.

For working up, the mixture is cooled to about 100° C., water is added and the batch is shaken repeatedly with a water-immiscible solvent. The combined organic extracts are washed with dilute sodium hydroxide solution and water, and after stripping off the solvent in vacuo the crude product which remains is purified by vacuum distillation. The purity criteria used are the gas chromatogram, boiling point and refractive index.

When working with sodium phenolate in the presence of a potassium salt, in general between 1 and 3, preferably about 1.05 to 1.5, moles of sodium phenolate and about 0.1 to 2, preferably about 0.4 to 1.5, moles of potassium salt, preferably potassium chloride, are employed per mole of 3-bromo-4-fluoro-toluene. The reaction is started in one of the above-mentioned solvents at a temperature of between 120° and 150° C. and is subsequently continued at 130° to 170° C. The catalyst is employed in an amount of between 0.001 and 0.1 mole, preferably between 0.005 and 0.05 mole, per mole of 3-bromo-4-fluoro-toluene. The reaction mixture is in general stirred at the required temperature for between 12 and 48 hours, preferably between 20 and 30 hours.

For working up, the mixture is cooled, stirred with a water-immiscible solvent and kieselguhr, and filtered. The filtrate is washed with dilute sodium hydroxide solution and water, the solvent is stripped off in vacuo and the crude product which remains is distilled in a high vacuum. The purity criteria used are the gas chromatogram, boiling point and refractive index.

The 4-fluoro-3-phenoxy-toluene prepared by the process according to the invention can be used (See DE-OS [German Published Specification] No. 2,709,264) as an intermediate product for the preparation of insecticidally and acaricidally active 4-fluoro-3-phenoxy-benzyloxy-carbonyl compounds of the general formula

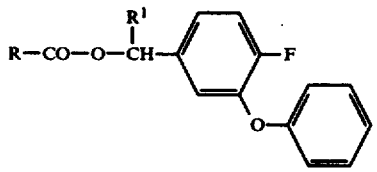

(III), in which R represents the radical

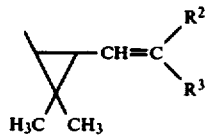

wherein $R^2$ and $R^3$, which may be identical or different, each represents chlorine, bromine or methyl, or in which R represents the radical

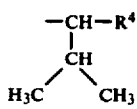

wherein $R^4$ represents phenyl which is optionally substituted by halogen, alkyl, alkoxy, alkylthio, nitro or methylenedioxy, and $R^1$ represents hydrogen, cyano or ethynyl.

Compounds of the formula (III) are in general obtained by reacting carboxylic acid chlorides of the general formula

 R—CO—Cl (IV), in which R has the above-mentioned meaning, with 4-fluoro-3-phenoxy-benzyl alcohols of the general formula

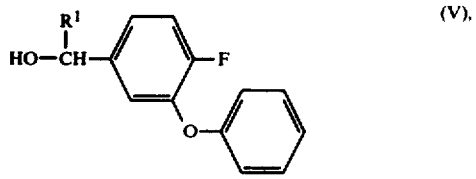

in which $R^1$ has the above-mentioned meaning, if appropriate in the presence of an acid acceptor and, if appropriate, using a diluent.

For example, 2,2-dimethyl-3-(2,2-dichlorovinyl)-cyclopropanecarboxylic acid α-cyano-4-fluoro-3-phenoxy-benzyl ester is obtained by reacting 2,2-dimethyl-3-(2,2-dichlorovinyl)-cyclopropanecarboxylic acid chloride with α-cyano-4-fluoro-3-phenoxy-benzyl alcohol in the presence of equimolar amounts of pyridine as the acid acceptor, and using toluene as the diluent, at temperatures between 0° and 50° C., preferably at from 20° to 30° C., in accordance with the following equation:

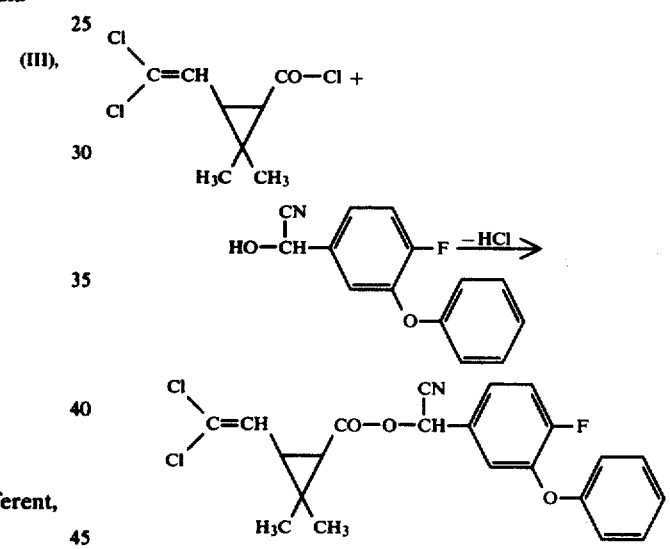

4-Fluoro-3-phenoxy-benzyl alcohols of the formula (V) can be prepared from the 4-fluoro-3-phenoxy-toluene, obtainable according to the invention, by various methods known from the literature, via several stages.

For example, 4-fluoro-3-phenoxy-toluene, when reacted with N-bromosuccinimide in the presence of a radical initiator, for example azodiisobutyronitrile, optionally using a diluent, for example carbon tetrachloride, optionally using a diluent, and 100° C., gives 4-fluoro-3-phenoxy-benzyl bromide. From this, 4-fluoro-3-phenoxy-benzaldehyde can be prepared in a Sommelet reaction, that is to say by reaction with hexamethylenetetramine in the presence of a diluent, for example methylene chloride, at temperatures between 0° and 50° C., followed by reaction with aqueous acetic acid and thereafter with hydrochloric acid, at temperatures between 80° and 120° C. The reaction of 4-fluoro-3-phenoxy-benzaldehyde with sodium cyanide in aqueous acetic acid at 20° C. gives α-cyano-4-fluoro-3-phenoxy-benzyl alcohol. The reaction sequence described above is outlined in the following equations:

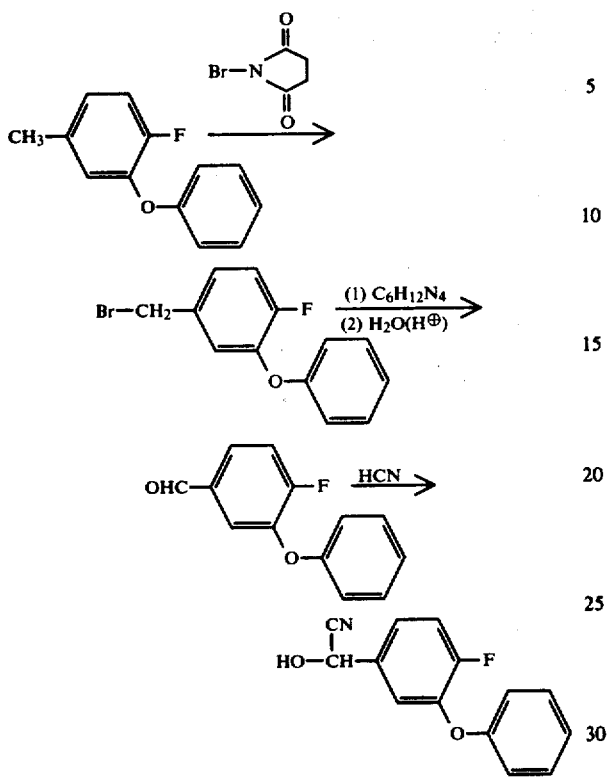

4-Fluoro-3-phenoxybenzyl alcohol and α-ethynyl-4-fluoro-3-phenoxy-benzyl alcohol are obtained from 4-fluoro-3-phenoxy-benzaldehyde by, for example, reaction with lithium aluminum hydride and ethynylmagnesium bromide, respectively, in accordance with known methods.

The use of the 4-fluoro-3-phenoxy-benzyloxy-carbonyl compounds of the formula (III), which may be prepared starting from 4-fluoro-3-phenoxy-toluene, as insecticides and acaricides is the subject of DE-OS [German Published Specification] No. 2,709,264.

The process of the present invention is illustrated by the following preparative examples.

EXAMPLE 1

128 g of N,N-dimethylacetamide were heated to 130°-140° C. in a 1 liter three-necked flask. At this temperature, 128 g of sodium phenolate (1.1 mole) were introduced, while stirring. Furthermore, 76 g of potassium chloride and 1 g of copper oxide were added to the solution. 189.1 g (1 mole) of 3-bromo-4-fluoro-toluene were allowed to run into the stirred mixture at 140° C. in the course of about 10 minutes. A temperature of 150°-155° C. was maintained for 24 hours while stirring. After cooling, the contents of the flask were stirred with 800 ml of ligroin and 40 g of kieselguhr. The mixture was filtered, the filter residue was rinsed with ligroin, and the filtrate was shaken with 400 ml of 10% strength sodium hydroxide solution. After the filtrate had been washed with water until neutral, the solvent was removed in vacuo and the residue was distilled in vacuo; this gave 142.5 g of a colorless liquid of boiling point 94°-96° C./2 mm Hg ($n_D^{22}$:1.5559). The yield of 4-fluoro-3-phenoxy-toluene was 70.5% of theory, relative to the bromofluorotoluene employed.

EXAMPLE 2

141.2 g (1.5 mole) of phenol, 1.5 mole of potassium hydroxide and 500 ml of xylene were mixed in a 1 liter stirred flask. The mixture was dehydrated by boiling under a water separator, until about 32 ml of water had been separated off. The solvent was then distilled off in vacuo and 150 ml of N,N-dimethylacetamide and 0.5 g of copper oxide were added. 94.2 g (0.5 mole) of 3-bromo-4-fluoro-toluene were run in over the course of about 5 minutes at an internal temperature of 140°-145° C., while stirring, and stirring was continued for 4 hours at this temperature. After cooling to 100° C., 350 ml of water were added. The mixture was extracted by shaking at room temperature with three 200 ml portions of ligroin, and the collected extract was washed with dilute sodium hydroxide solution and water. The solvent was stripped off in vacuo and the residue was distilled. This gave 81.9 g of a colorless liquid of boiling point 94°-96° C./2 mm Hg ($n_D^{22}$:1.5555). The yield of 4-fluoro-3-phenoxy-toluene was 81% of theory, relative to the bromofluorotoluene employed.

It will be appreciated that the instant specification and examples are set forth by way of illustration and not limitation, and that various modifications and changes may be made without departing from the spirit and scope of the present invention.

What we claim is:

1. A process for the preparation of 4-fluoro-3-phenoxy-toluene of the formula

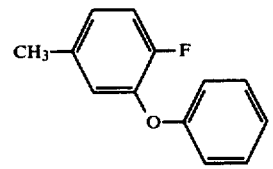

comprising reacting 3-bromo-4-fluoro-toluene, of the formula

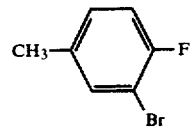

with potassium phenolate, or with sodium phenolate in the presence of a potassium salt, in a diluent in the presence of copper as catalyst at a temperature between about 120° and 180° C.

2. A process according to claim 1, wherein the reaction is effected at a temperature between about 130° and 170° C.

3. A process according to claim 1, wherein the catalyst is copper, copper(I) oxide, copper(II) oxide, copper(I) chloride, copper(II) chloride, copper(I) bromide, copper(II) bromide or copper(I) iodide.

4. A process according to claim 1, wherein the diluent is an aprotic polar solvent.

5. A process according to claim 4, wherein the solvent is a carboxylic acid amide, a sulphoxide, a sulphone or a phosphoric acid amide.

6. A process according to claim 5, wherein the solvent is dimethylacetamide.

7. A process according to claim 1, wherein about 0.001 to 0.1 mole of catalyst is employed per mole of 3-bromo-4-fluoro-toluene.

8. A process according to claim 7, wherein about 0.005 to 0.05 mole of catalyst is employed per mole of 3-bromo-4-fluoro-toluene.

9. A process according to claim 1, wherein there are employed about 1.5 to 8 moles of potassium phenolate per mole of 3-bromo-4-fluoro-toluene.

10. A process according to claim 9, wherein about 2 to 4 moles of potassium phenolate are employed per mole of 3-bromo-4-fluoro-toluene.

11. A process according to claim 1, wherein there are employed about 1 to 3 moles of sodium phenolate and about 0.1 to 2 moles of a potassium salt per mole of 3-bromo-4-fluoro-toluene.

12. A process according to claim 11, whereabout about 1.05 to 1.5 moles of sodium phenolate and about 0.4 to 1.5 moles of the potassium salt are employed per mole of 3-bromo-4-fluoro-toluene.

13. A process according to claim 11, wherein the potassium salt is potassium chloride.

14. A process according to claim 3, wherein the reaction is effected at a temperature between about 130° and 170° C., the diluent is dimethylacetamide, and per mole of 3-bromo-4-fluoro-toluene there are employed about 0.005 to 0.5 mole of catalyst, and (a) about 2 to 4 moles of potassium phenolate or (b) about 1.05 to 1.5 moles of sodium phenolate and about 0.4 to 1.5 moles of potassium chloride.

* * * * *